(12) United States Patent
Roorda

(10) Patent No.: US 9,248,121 B2
(45) Date of Patent: *Feb. 2, 2016

(54) MEDICAL DEVICES FOR CONTROLLED DRUG RELEASE

(75) Inventor: Wouter Roorda, Palo Alto, CA (US)

(73) Assignee: ABBOTT LABORATORIES, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/839,093

(22) Filed: Aug. 15, 2007

(65) Prior Publication Data

US 2008/0057101 A1 Mar. 6, 2008

Related U.S. Application Data

(60) Provisional application No. 60/823,057, filed on Aug. 21, 2006, provisional application No. 60/823,061, filed on Aug. 21, 2006, provisional application No. 60/823,063, filed on Aug. 21, 2006, provisional application No. 60/823,067, filed on Aug. 21, 2006, provisional application No. 60/823,069, filed on Aug. 21, 2006, provisional application No. 60/823,071, filed on Aug. 21, 2006.

(51) Int. Cl.
*A61K 31/436* (2006.01)
*A61K 9/00* (2006.01)
*A61L 31/14* (2006.01)
*A61L 31/16* (2006.01)

(52) U.S. Cl.
CPC ............ *A61K 31/436* (2013.01); *A61L 31/146* (2013.01); *A61L 31/16* (2013.01); *A61F 2250/0068* (2013.01); *A61L 2300/608* (2013.01)

(58) Field of Classification Search
CPC ............ A61F 2250/0068; A61K 31/436; A61L 2300/608; A61L 31/146; A61L 31/16
USPC ............ 424/400, 425, 427, 484; 514/291
See application file for complete search history.

(56) References Cited

U.S. PATENT DOCUMENTS

| | | | |
|---|---|---|---|
| 4,612,160 A | 9/1986 | Donlevy et al. | |
| 5,705,583 A | 1/1998 | Bowers et al. | |
| 5,843,172 A | 12/1998 | Yan | |
| 6,083,257 A | 7/2000 | Taylor et al. | |
| 6,090,901 A | 7/2000 | Bowers et al. | |
| 6,240,616 B1 | 6/2001 | Yan | |
| 6,273,913 B1 | 8/2001 | Wright et al. | |
| 6,287,628 B1 | 9/2001 | Hossainy et al. | |
| 6,379,381 B1 | 4/2002 | Hossainy et al. | |
| 6,527,938 B2 | 3/2003 | Bales et al. | |
| 6,652,581 B1* | 11/2003 | Ding | 623/1.39 |
| 6,663,662 B2* | 12/2003 | Pacetti et al. | 623/1.13 |
| 6,723,120 B2 | 4/2004 | Yan | |
| 6,945,448 B2 | 9/2005 | Medlin et al. | |
| 7,077,859 B2* | 7/2006 | Sirhan et al. | 623/1.15 |
| 7,179,288 B2 | 2/2007 | Shanley | |
| 7,208,010 B2 | 4/2007 | Shanley et al. | |
| 7,335,314 B2 | 2/2008 | Wu et al. | |
| 7,699,832 B2* | 4/2010 | Dinh et al. | 604/890.1 |
| 7,699,890 B2 | 4/2010 | Yan | |
| 7,931,931 B2 | 4/2011 | Yan | |
| 2001/0013166 A1 | 8/2001 | Yan | |
| 2002/0133224 A1 | 9/2002 | Bajgar et al. | |
| 2004/0088038 A1 | 5/2004 | Dehnad et al. | |
| 2004/0143322 A1 | 7/2004 | Litvack et al. | |
| 2005/0048193 A1 | 3/2005 | Li et al. | |
| 2005/0107869 A1 | 5/2005 | Sirhan et al. | |
| 2005/0119723 A1 | 6/2005 | Peacock, III | |
| 2005/0209680 A1 | 9/2005 | Gale et al. | |
| 2005/0220853 A1 | 10/2005 | Dao et al. | |
| 2005/0266040 A1 | 12/2005 | Gerberding | |
| 2005/0283229 A1 | 12/2005 | Dugan et al. | |
| 2006/0026815 A1* | 2/2006 | Padilla et al. | 29/558 |
| 2006/0121080 A1 | 6/2006 | Lye et al. | |
| 2007/0003749 A1 | 1/2007 | Asgari | |
| 2007/0189915 A1 | 8/2007 | Shrivastava et al. | |
| 2007/0191943 A1 | 8/2007 | Shrivastava et al. | |
| 2007/0258903 A1 | 11/2007 | Kleiner et al. | |
| 2007/0259101 A1* | 11/2007 | Kleiner et al. | 427/2.24 |
| 2008/0051335 A1 | 2/2008 | Kleiner et al. | |
| 2008/0057102 A1 | 3/2008 | Roorda et al. | |
| 2008/0057103 A1 | 3/2008 | Roorda et al. | |
| 2008/0288058 A1 | 11/2008 | Yan | |

FOREIGN PATENT DOCUMENTS

WO WO 2007/145961 12/2007

OTHER PUBLICATIONS

Bhargava et al., "New Approaches to Preventing Restenosis", BMJ vol. 327, pp. 274-279 (2003).

(Continued)

*Primary Examiner* — Janet Epps-Smith
*Assistant Examiner* — Courtney Brown
(74) *Attorney, Agent, or Firm* — Squire Patton Boggs (US) LLP

(57) ABSTRACT

The present invention is a medical device for controlling the release of an active agent. The medical device has a supporting structure having a porous body disposed therein. At least one elution rate controlling matrix containing an effective amount of at least one active agent is disposed within the pores of the porous body in a manner that protects the matrix from mechanical damage. The medical device may therefore be used for controlled drug release applications. Additionally, the present invention discloses a method for using the medical device for the treatment and prevention of diseases in mammals. This invention further relates to a method for using the medical device for treating and preventing vascular diseases.

13 Claims, 3 Drawing Sheets

(56) References Cited

OTHER PUBLICATIONS

Landers et al., "Desktop manufacturing of complex objects, prototypes and biomedical scaffolds by means of computer-assisted design combined with computer-guided 3D plotting of polymers and reactive oligomers," Macromaol. Mater. Eng. 2000, vol. 282, pp. 17-21.

Waurzyniak, Patrick "Rapid Metal" Manugacturing Engineering, vol. 131, No. 5, 2003, pp. 1-5.

USPTO, Office Action dated Aug. 28, 2012 in U.S. Appl. No. 11/839,121, 32 pages total.

* cited by examiner

MEDICAL DEVICES FOR CONTROLLED DRUG RELEASE

CROSS-REFERENCE TO RELATED APPLICATIONS

This U.S. patent application claims benefit of U.S. provisional patent applications having Ser. Nos. 60/823,057, 60/823,061, 60/823,063, 60/823,067, 60/823,069 and 60823,071 each filed on Aug. 21, 2006, each entitled "MEDICAL DEVICES FOR CONTROLLED DRUG RELEASE", and each having Wouter Roorda as the inventor, which U.S. provisional patent applications are incorporated herein in their entirety by specific reference. Additionally, this U.S. patent application cross-references related U.S. patent applications filed herewith and having Ser. Nos. 11/839,104 filed Aug. 15, 2007 entitled "METHODS OF MANUFACTURING MEDICAL DEVICES FOR CONTROLLED DRUG RELEASE", and 11/839,121 filed Aug. 15, 2007 entitled "METHODS OF USING MEDICAL DEVICES FOR CONTROLLED DRUG RELEASE", which cross-referenced applications are incorporated herein in their entirety by specific reference.

BACKGROUND

I. Technology Field

The present invention relates to medical devices, endoprostheses, stents, and methods for the manufacture and use of the same. More particularly, the devices of the present invention are configured to include a porous network that contains an elution rate controlling matrix carrying an active agent.

II. The Related Technology

Balloon angioplasty, either alone or followed by an endoprosthetic implantation, has become a commonplace interventional alternative to open heart surgery in those patients appropriate for such treatment. Endoprostheses are generally tubular members having a collapsed state suitable for insertion into a vessel and a deployed state in which the endoprosthesis is expanded to support the surrounding tissue and prevent at least local narrowing of the vessel. Several types of endoprostheses are known, including balloon expandable, self-expanding, and endoprostheses constructed from biostable springs.

Polymeric materials, for example, are commonly used in medical devices as matrices for the retention of therapeutic agents. These polymeric materials are typically applied as coatings to the medical devices, raising issues regarding coating adhesion, mechanical properties, cracking, delamination, and material biocompatibility. However, problems occur when mechanical forces are applied on an endoprosthesis during manufacture (e.g., crimping, endoprosthetic retention procedures, packaging etc.) as well as during actual use (e.g., unsheathing, catheter preparation, advancement through catheter and vasculature), which may result in damaging the polymeric coating. In addition, many polymers with desirable controlled release properties, like the family of biodegradable polymers based on polylactide, polyglycolide and their copolymers are difficult candidates for a polymeric endoprosthetic coating, because of poor adhesion to metals and/or poor elongation and brittle character.

There exists a need in the art for medical devices (specifically, drug eluting endoprostheses) capable of retaining a therapeutic agent in an endoprosthesis so that the drug may be eluted to a local region of the vessel wall in a controlled manner through pores in the endoprosthesis. Furthermore, an ideal medical device would incorporate agents within a polymer in protective pores to reduce or eliminate current aggressive manufacturing method problems or actual use to prevent physical damage of the medical device.

BRIEF SUMMARY

The present invention is a medical device for controlling the release of an active agent. The medical device has a supporting structure that is configured and dimensioned to be used within a body of an animal. The medical device of the present invention has a porous body disposed on and at least partially covering the supporting structure of the medical device. The porous body is made from a biocompatible material having a plurality of pores.

In one embodiment, the present invention includes a medical device for controlling the release of an active agent therefrom. Such a medical device can include the following: a supporting structure configured and dimensioned to be used within a body of an animal; a porous body disposed on and at least partially covering the supporting structure, said porous body including a first biocompatible material having a plurality of pores; a therapeutically effective amount of an active agent disposed within at least a portion of the pores, said therapeutically effective amount of the active agent being capable of treating and/or preventing a disease; and an elution rate controlling matrix disposed on at least one surface of the porous body so as to contain the active agent within said at least a portion of the pores, said matrix including a second biocompatible material that controls an elution rate of the active agent from the pores.

In one embodiment, the present invention includes an endoprosthesis for controlling the release of an active agent therefrom. Such an endoprosthesis can include the following: a supporting metal structure configured and dimensioned to be used within a body of a human; a porous body disposed on and at least partially covering the supporting metal structure, said porous body including a first biocompatible material having a plurality of pores; a therapeutically effective amount of an active agent disposed within said pores, said therapeutically effective amount of the active agent being capable of treating and/or preventing a disease; an elution rate controlling matrix disposed within the porous body so as to contain said active agent within said pores, said matrix material including a polymeric biocompatible material that at least partially controls an elution rate of the active agent from the pores; and said pores each having a dimension that is configured to at least partially determine said elution rate.

In one embodiment, the present invention includes a stent for controlling the release of an active agent therefrom. Such a stent can include the following: a superelastic metal structure configured and dimensioned as a stent to be used within a lumen of an animal; a porous body disposed on and at least partially covering the superelastic metal structure, said porous body including a first biocompatible material having a plurality of pores; a therapeutically effective amount of an active agent disposed within at least a portion of the pores, said therapeutically effective amount of the active agent being capable of treating and/or preventing a disease; and an elution rate controlling matrix disposed on at least one surface of the porous body so as to contain the active agent within said at least a portion of the pores, said matrix material including a second biocompatible material that controls an elution rate of the active agent from the pores. Optionally, the porous body is integrated with the supporting structure.

In one embodiment, the porous body has a thickness ranging from about 10 nanometers to about 1 millimeter. Also, the porous body can include pores having a diameter of from about 10 nanometers to about 1 millimeter.

In one embodiment, the medical device is selected from the group consisting of endoprostheses, drug delivery stents, drug delivery catheters, grafts, drug delivery balloons, guidewires, orthopedic implants, dental implants, fixation screws, indwelling catheters, ocular implants, pharmacotherapeutic implants, blood-contacting components of extracorporeal devices, staples, filters, needles, tubes, coils, wires, clips, screws, sensors, plates, conduits, portions thereof, and combinations thereof.

In one embodiment, the second biocompatible material is at least one polymeric material comprised of phosphorylcholines, phosphorylcholine linked macromolecules, polyolefins, poly(meth)acrylates, polyurethanes, polyesters, polyanhydrides, polyphosphazenes, polyacrylates, acrylic polymers, poly(lactide-coglycolides) (PLGA), polylactic acids (PLA), poly(hydroxybutyrates), poly(hydroxybutyrate-co-valerates), polydioxanones (PDO), polyorthoesters, polyglycolic acids (PGA), polycaprolactones (PCL), poly(glycolic acid-co-trimethylene carbonates), polyphosphoesters, polyphosphoester urethanes, poly(amino acids), cyanoacrylates, poly(trimethylene carbonate), poly(iminocarbonate), polyalkylene oxalates, polyiminocarbonates, aliphatic polycarbonates, fibrins, fibrinogens, celluloses, starchs, collagens, polycarbonate urethanes, polyisoprenes, polyisobutylenes, polybutadienes, polyethylenes, plasticized polyethylene terephthalates, polyethylene terepthalates, polymethylmethacrylates, ethylene ethylacrylates, polyethyl hexylacrylates, plasticized ethylene vinylacetates, polyvinyl acetates, ethylene vinyl acetates, ethylene vinyl alcohols, polyvinyl alcohols, cross-linked polyvinyl alcohols, cross-linked polyvinyl butyrates, polyvinylbutyrates, polybutylmethacrylates, polyvinyl chlorides, ethylene vinylchloride copolymers, silicones, polysiloxanes, substituted polysiloxanes, polyethylene oxides, polyethylene glycols (PEG), polybutylene terepthalate-co-PEG, PCL-co-PEG, PLA-co-PEG, polyvinyl acetals, polyvinyl acetates, polyamides, polyvinyl pyrrolidones, polyacrylamides, polyvinyl esters, copolymers thereof, polymer derivatives thereof, or combinations thereof.

In one embodiment, the active agent is comprised of at least one of analgesics, antipyretics, antiasthamatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, or combinations thereof. Preferably, the active agent comprises at least one of rapamycin, rapamycin analog, zotarolimus, sirolimus, everolimus, dexamethasone, prednisone, hydrocortisone, estradiol, acetaminophen, ibuprofen, naproxen, sulidac, heparin, taxol, paclitaxel, and combinations thereof.

In one embodiment, the present invention includes a method of treating and/or preventing a disease in an animal. Such as method can include the following: providing a medical device (e.g., endoprosthesis, stent, etc.) configured and dimensioned to be used within a body of an animal, as described herein; deploying the medical device into the body of the animal; and allowing the active agent to elute from the pores into the body of the animal, where the elution rate controlling matrix controls the elution of the active agent from the pores. Accordingly, the medical device can be placed into or in contact with a body or fluid of an animal. This can include placing the medical device within the vascular system of an animal. The medical device can then elute a therapeutically effective amount of the active agent to treat and/or prevent a disease in which said active agent is useful as a therapy. For example, the medical device can treat a vascular disease, such as restenosis.

In one embodiment, the present invention includes a method of manufacturing a medical device used for treating and/or preventing a disease in an animal. Such a method can include the following: fabricating a supporting structure, which can include shaping the supporting structure into the medical device (e.g., endoprosthesis, stent, etc.); fabricating a porous body onto at least a portion of the supporting structure, said porous body including a first biocompatible material having a plurality of pores; introducing a therapeutically effective amount of an active agent into at least a portion of the pores, said therapeutically effective amount of the active agent being capable of treating and/or preventing a disease; and introducing an elution rate controlling matrix onto at least one surface of the porous body so as to contain the active agent within said at least a portion of the pores, said matrix including a second biocompatible material that controls the elution of the active agent from the pores.

In one embodiment, the fabrication of the porous body can include dimensioning and configuring the porous body to have a thickness ranging from about 10 nanometers to about 1 millimeter. Also, the fabrication of the porous body can include dimensioning and configuring the pores to have a diameter of from about 10 nanometers to about 1 millimeter.

In one embodiment, the method of manufacture can include configuring the medical device to be at least one of an endoprosthesis, drug delivery stent, drug delivery catheter, graft, drug delivery balloon, guidewire, orthopedic implant, dental implant, fixation screws, indwelling catheter, ocular implant, pharmacotherapeutic implant, blood-contacting component of extracorporeal device, staple, filter, needle, tube, coil, wire, clip, screw, sensor, plate, conduit, portion thereof, or combination thereof.

In one embodiment, the method of manufacture can include combining the active agent with the second biocompatible material. This can include combining the active agent and elution rate controlling matrix before, during, or after being introduced into the porous body. As such, the active agent can be absorbed into the elution rate controlling matrix after being introduced into the porous body.

In one embodiment, the method of manufacture can include any of the following processes: fabricating the supporting structure and/or porous body by sintering; fabricating the supporting structure and/or porous body by a metal printing process; fabricating the supporting structure and/or porous body by a direct rapid prototyping process; or shaping the supporting structure and/or porous body into an endoprosthesis.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments which are illustrated schematically in the accompanying drawings and in the appended claims.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF PREFERRED EMBODIMENTS

Figure 1:
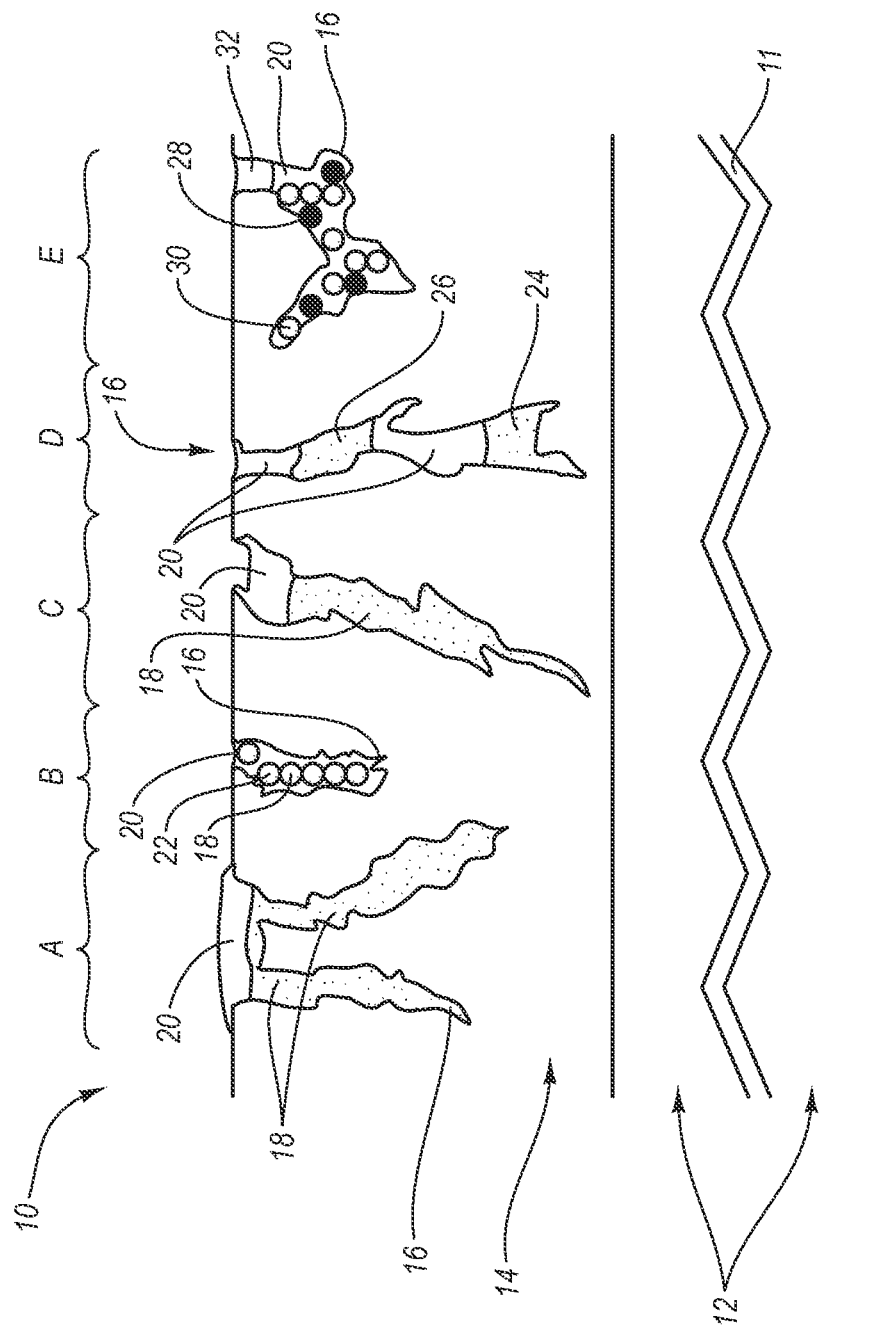
FIG. 1 is a cross-sectional view illustrating an embodiment of a portion of a medical device including a supporting structure defining a lumen and having a porous body disposed thereon, wherein different pore embodiments are depicted to have different active agent and elution rate controlling matrix embodiments.

The present invention generally relates to a drug eluting medical devices, endoprostheses, stents, and the like that have an elution rate controlling matrix that contains an active agent and that is disposed within a porous material. Also, the present invention relates to methods of manufacturing and using the medical devices of the invention in treating and/or preventing diseases in animals, such as mammals. The medical devices of the invention are constructed of materials suitable for use in animals, and include at least one elution rate controlling matrix and a therapeutically effective amount of at least one biologically active agent. The medical devices of the invention also include at least one porous material associated with a supporting structure, where the elution rate controlling matrix containing the active agent is disposed within the pores of the porous material. The pores of the porous material can be dimensioned and configured to cooperate with the elution rate controlling matrix for controlling the elution of the active agent.

Drug eluting medical devices, such as endoprostheses (e.g., stents), are known in the art, but a problem with the use of existing medical devices having drug eluting coatings is that the coatings are prone to being rubbed off or otherwise damaged during the manufacturing processes, through manipulation by the physician, during the deployment procedure, or through scratching, rubbing, or other interactions with the body in which they are deployed. One additional problem with drug eluting medical devices has been the lack of being able to control the rate of elution of the drugs from the coatings.

An advantage for a medical device of the present invention includes the polymer containing an active agent being resistant to damage from mechanical forces placed upon an endoprosthesis during manufacture (e.g. crimping, endoprosthesis retention procedures, and packaging) as well as during actual use (e.g. unsheathing, catheter prep, advancement through catheter, and vasculature). In part, this is because the elution rate controlling matrix is disposed inside the protective pores of a porous body, making more manufacturing methods possible. For example, with small, densely dispersed pores, a fairly uniform distribution of the matrix is achieved. As such, the porous body can protect the matrix from mechanical damage such as delamination, flaking, and/or cracking.

Another advantage permits the use of many polymers (previously unusable) with desirable controlled release properties including biodegradable polymers based on polylactide and/or polyglycolide. Polylactide and/or polyglycolide polymers are difficult candidates for a drug elution rate controlling coating because of their poor adhesion to metals and/or poor elongation and brittle character. By incorporating agents within polylactide and/or polyglycolide, and by incorporating the mixture within the pores of the porous body of the medical devices, the use of polylactide and/or polyglycolide polymers, for example, becomes feasible.

I. Introduction

The medical devices of the present invention are configured to be capable of controlling the elution of active agents (e.g., pharmaceuticals, therapeutics, and other substances or compounds) from the medical device. As such, the medical device is configured for either permanent or temporary placement into, or brought in contact with, the body or body fluid of an animal. The medical device is constructed to include supporting structure for a porous body that includes at least one elution rate controlling matrix containing an effective amount of at least one active agent. The porous body has a plurality of pores that are dimensioned and configured to retain the elution rate controlling matrix, and for contributing to the controlled elution profile of the active agent. Thus, the porous body and the elution rate controlling matrix are configured, either individually or in combination, to control the release of the active agent in order to achieve the desired diffusion kinetics.

The medical device is constructed of at least one biocompatible material. That is, the different portions of the medical device can be constructed of different biocompatible materials, which can be different types of metals, polymers, or ceramics, or different combinations of such materials. For example, the supporting structure and porous body can be prepared of different types of metals, while the elution rate controlling matrix can be prepared from a polymer. In some medical devices, the supporting structure and/or porous body can be prepared from a shape-memory material.

The porous body of the medical device can include millipores, micropores, and/or nanopores. The dimension of the pores can be modulated and adapted for the particular needs and uses of the medical device on which it will be utilized. In any event, the pores are configured to be capable of retaining the elution rate controlling matrix and allowing for the elution of the active agent therefrom with controlled diffusion kinetics. As such, the pores can be configured to obtain zero, first, and/or second order diffusion kinetics with or without burst effects.

Additionally, the configuration of the medical devices that includes the elution rate controlling matrix disposed within the pores of the porous body can allow for a broader range of polymers to be used in the matrix. The porous body provides increased resistance to physical damage of the elution rate controlling matrix and agents disposed therein That is, the disposition of the matrix in the pores protects the matrix in a manner that allows for structurally weak polymers that are subject to uncontrolled degradation by physical contact to now be usable with drug eluting medical devices. As such, polymers not previously available for use as drug eluting materials can now be used in drug eluting medical devices. In part, this is because the porous body protects the elution rate controlling matrix from contact with the body of a patient (e.g., intraluminal wall). Therefore, polymer coatings of a polymer-coated medical device that would normally rub off or otherwise uncontrollably degrade are able to maintain structural integrity by being protected by the porous body.

A. Definitions

The terms "agent" refers to an active agent that has biological activity and may be used in a therapy. Also, an "agent" can be synonymous with "at least one agent," "compound," or "at least one compound," and can refer to any form of the agent, such as a derivative, analog, salt or a prodrug thereof. The agent can be present in various forms, components of molecular complexes, and pharmaceutically acceptable salts (e.g., hydrochlorides, hydrobromides, sulfates, phosphates, nitrates, borates, acetates, maleates, tartrates, and silicylates). The term "agent" can also refer to any pharmaceutical molecules or compounds, therapeutic molecules or compounds, matrix forming molecules or compounds, polymers, synthetic molecules and compounds, natural molecules and compounds, and any combination thereof.

The terms "an effective amount" or "therapeutically effective amount" of an agent, compound or therapeutic, with respect to methods of treatment, refers to an amount of the pharmaceutical, therapeutic, agent or other compound in a preparation which, when administered as part of a desired dosage regimen (to an animal, preferably a human) alleviates a symptom, ameliorates a condition, or slows the onset of disease conditions according to clinically acceptable standards for the disorder or condition to be treated or the cosmetic purpose. A "therapeutically effective amount," as recognized by those of skill in the art, will be determined on a case by case basis. Factors to be considered include, but are not limited to, the disorder to be treated and the physical characteristics of the one suffering from the disorder.

The terms "biocompatible" and "biocompatibility" are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction at unacceptable levels in the host. It is not necessary that any subject composition have a purity of 100% to be deemed biocompatible. Hence, a subject composition may comprise 99%, 98%, 97%, 96%, 95%, 90%, 85%, 80%, 75%, or even less of biocompatible agents, such as polymers and other materials and excipients described herein, and still be biocompatible.

The term "co-incorporation" or "co-encapsulation" refers to the incorporation of a pharmaceutical, therapeutic, agent, compound, or other material, and at least one other pharmaceutical, therapeutic, agent, compound, or other material in an elution rate controlling matrix. More specifically, the physical form in which any pharmaceutical, therapeutic agent, compound or other material is encapsulated in an elution rate controlling matrix may vary with the particular embodiment. For example, a pharmaceutical, therapeutic, agent, compound, or other material may be first encapsulated in a microsphere and then combined with the elution rate controlling matrix in such a way that at least a portion of the microsphere structure is maintained. Alternatively, a pharmaceutical, therapeutic, agent, compound, or other material may be sufficiently immiscible in the polymer of the invention such that it is dispersed as small droplets, rather than being dissolved, in the elution rate controlling matrix. Any form of encapsulation or incorporation is contemplated by the invention, in so much as the release, or sustained release, of any encapsulated pharmaceutical, therapeutic, agent, compound, or other material determines whether the form of encapsulation is sufficiently acceptable for any particular use.

The term "dispersed" means at least one bioactive agent and/or compound as disclosed herein is dispersed, mixed, dissolved, homogenized, and/or covalently bound ("dispersed") in a polymer, such as the elution rate controlling matrix.

The term "encapsulation" or "incorporation" when used in reference to a pharmaceutical, therapeutic, agent, compound, or other material and an elution rate controlling matrix indicates that the agent is contained within the elution rate controlling matrix. In certain embodiments, these terms include incorporating, formulating, or otherwise including such agents into a composition that allows for release, such as sustained release, of such agent in the desired application. The terms contemplate any manner by which a pharmaceutical, therapeutic, agent, compound, or other material is incorporated into a polymer matrix, including for example: attached to a monomer of such elution rate controlling matrix (e.g., by covalent, ionic, or other binding interaction), physical admixture, enveloping the agent in a coating layer of a polymer, and having such monomer be part of the polymerization to give a polymeric formulation, distributed throughout the polymeric matrix, appended to the surface of the polymeric matrix (e.g., by covalent or other binding interactions), encapsulated inside the polymeric matrix (e.g., elution rate controlling matrix), and the like.

The term "pharmaceutically acceptable salts" is art-recognized, and includes relatively non-toxic, inorganic and organic acid, or base addition salts of compositions, including without limitation, analgesic agents, therapeutic agents, other materials, and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc, and the like. Salts may also be formed with suitable organic bases, including those that are non-toxic and strong enough to form such salts. For purposes of illustration, the class of such organic bases may include mono-, di-, and trialkylamines, including methylamine, dimethylamine, and triethylamine; mono-, di-, or trihydroxyalkylamines including mono-, di-, and triethanolamine; amino acids, including arginine and lysine; guanidine; N-methylglucosamine; N-methylglucamine; L-glutamine; N-methylpiperazine; morpholine; ethylenediamine; N-benzylphenethylamine; tri-hydroxymethyl aminoethane; and the like. (See, J. Pharm. Sci. 66: 1-19 (1977)).

The term "polymer" is intended to include a product of a polymerization reaction inclusive of oligomers, homopolymers, copolymers, terpolymers, and the like, whether natural or synthetic, including random, alternating, block, graft, branched, cross-linked, blends, compositions of blends, and variations thereof.

The term "pharmaceutically acceptable carrier" means a non-toxic solid, semi-solid or liquid filler, diluent, encapsulating material, or formulation auxiliary of any type.

The term "preventing" or "prevention" is art-recognized, and when used in relation to a condition, including a local recurrence (e.g., pain), a disease including cancer, a syndrome complex including heart failure, or any other medical condition, is well understood in the art and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, (e.g., by a statistically and/or clinically significant amount). Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "metal," as used herein, refers to elemental metals, alloys of elemental metals, alloys having multiple components, and metals mixed with other elements or compounds in a heterogeneous or homogeneous mixture.

The term "pore," as used herein, refers to invaginations in a surface such that one end of the pore is exposed to the surface and the other end of the pore is disposed within the material whose surface the pore is displaced within. For example, a pore can be substantially hole-like, having a first end disposed within a metal covering of an endoprosthesis and having a second end forming an opening upon the surface of the metal covering of the endoprosthesis.

The term "porous layer," as used herein, refers to a layer having at least one pore. The porous layer is disposed upon another surface. The porous layer may have pores of different shapes. Also, the term "porosity" is art-recognized, and refers to both the void volume of a porous material as well as its surface area. It should be understood that a numerical value for porosity of a material, for instance as a percent of the total volume of material, can describe a wide range of compositions, since it does not include the surface area of the material. For example, a material with 50% porosity could have a small number of large pores, or a large number of small pores. The surface area of the latter can be many orders of magnitude larger than that of the former.

The term "pro-drug," as used herein, refers to compounds which are transformed in vivo to the parent compound of the formula above, for example, by hydrolysis in blood.

The term "sustained release," when used with respect to a pharmaceutical, therapeutic, agent, compound, or other material is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, lymph, or the like, the polymer matrices (formulated as provided herein and otherwise as known to one of skill in the art) may undergo gradual degradation (e.g., through hydrolysis) with concomitant release of any material incorporated therein (e.g., a therapeutic and/or biologically active agent) for a sustained or extended period as compared to the release from a bolus or burst effect. This release may result in prolonged delivery of therapeutically effective amounts of any incorporated therapeutic agent. Sustained release will vary in certain embodiments as described in greater detail below.

The term "treating" or "treatment" is art-recognized and includes preventing a disease, disorder or condition from occurring in an animal which may be predisposed to the disease, disorder, and/or condition but has not yet been diagnosed as having it; inhibiting the disease, disorder, or condition, impeding its progress; and relieving the disease, disorder, or condition (e.g., causing regression of the disease, disorder, and/or condition). Treating the disease or condition includes ameliorating at least one symptom of the particular disease or condition, even if the underlying pathophysiology is not affected, including treating the pain of a subject by administration of an analgesic agent even though such an agent does not treat the cause of the pain.

II. Medical Devices

In one embodiment, the present invention includes a medical device that is configured for controlling the release of an active agent therefrom. This can include release into a blood, organ, tissue, or other body fluid that is directed to circulate within a body. Such a medical device can include a supporting structure, porous body, elution rate controlling matrix, and an active agent. The supporting structure can be configured and dimensioned to be used within a body of an animal, or to be used in contact with a body fluid, organ, tissue, or other fluid that is directed to circulate within a body. The porous body can be disposed on and at least partially covering the supporting structure. Also, the porous body can be comprised of a first biocompatible material that is configured to include a plurality of pores or a porous network. The elution rate controlling matrix can be disposed on at least one surface of the porous body so as to contain the active agent within a portion of the pores. That is, the matrix can be disposed within the pores and adhered or affixed to the wall of a pore. The matrix material can be prepared from a second biocompatible material that determines an elution rate of the active agent from the pores. The active agent can be present in the matrix at a therapeutically effective amount that is being capable of treating and/or preventing a disease in which the medical device is used in an a therapy.

For example, the porous body has a thickness ranging from about 10 nanometers to about 1 millimeter, more preferably from about 100 nanometers to about 100 microns, more referable from about 1 micron to about 10 microns. Also, the porous body comprises pores having a diameter of from about 10 nanometers to about 1 millimeter, more preferably from about 100 nanometers to about 100 microns, more preferable from about 1 micron to about 10 microns. Also, the porous body can include a relative porosity from about 5% to about 98%, more preferably from about 40% to about 85%, and most preferably from about 50% to about 75%.

In one embodiment, the present invention is a drug eluting stent allowing for the controlled release of pharmaceutical and therapeutic agents. The stent includes at least one body having a lumen. The body is dimensioned into a desired stent configuration, and has at least one elution rate controlling material and an effective amount of at least one agent. The stent also has a layer of porous material associated with the stent body. The pores of the porous material are dimensioned and configured to house the elution rate controlling materials and agents for a controlled drug release application. The pores and elution rate controlling materials can be configured independently or in combination to control the release of the active agents therefrom.

In one embodiment, the active agents are homogeneously dispersed within the elution rate controlling matrix within the pores. The active agents may also be non-homogeneously or heterogeneously distributed within the elution rate controlling matrix within the pores. The elution rate controlling matrix provide for controlled release of agents, which includes long-term or sustained release of an agent that is bioactive and that is eluted from pores in a controlled, determined, and configured manner over a desired, often extended, period of time.

In one embodiment, where the elution rate controlling matrix is a biodegradable polymer, the biodegradation rate of the polymer may be characterized by a release rate of the active agent. In such circumstances, the biodegradation rate depends on not only the chemical identity and physical characteristics of the polymer, but also on the identity of agents incorporated therein.

In one embodiment, the elution rate controlling matrix is a polymeric formulation that is configured to biodegrade within a period that is acceptable in the desired application. In certain embodiments, including in vivo therapy, such degradation occurs in a period usually less than about five years, one year, six months, three months, one month, fifteen days, five days, three days, or even one day upon exposure to a physiological solution with a pH between 6 and 8 having a temperature of between 25 degrees Celsius and 37 degrees Celsius. In one embodiment, the polymer degrades in a period of between about one hour and several weeks.

FIG. 1 is a schematic representation of various embodiments of portions of a medical device 10 in accordance with the present invention. As such, the medical device 10 includes a supporting structure 12 that has a porous body 14 disposed thereon. In the illustrated embodiment, the medical device 10 is an endoprosthesis where the supporting structure 12 defines an internal lumen 11. However, the medical device 10 and supporting structure 12 can be configured into a wide array of shapes, sizes, and designs commensurate with the vast number of different types of medical devices.

The porous body 14 is shown to include a plurality of pores 16 that contain an active agent 18 and an elution rate controlling matrix 20. The pores 16 can have different shapes, sizes, and configurations depending on the process of manufacture as well as the desired functionality and desired elution rate of the active agent 18 from the matrix. As such, exemplary pore 16, active agent 18, and matrix 20 configurations are depicted in portions A-E.

Portion A shows that the active agent 18 can be deposed into a pore 16 and then covered with matrix 20, which forms a protective barrier for the active agent. Also, the matrix 20 serves to control the elution rate from the active agent 18 from the pore 16. As shown, the matrix 20 is disposed within the pore 16 in a manner such that a portion of the matrix 20 protrudes out of the pore 16.

Portion B shows the active agent 18 to be included within microspheres 22 that are disposed within the pore 16. Alternatively, the microspheres 22 can be microparticles, nanoparticles, or the like. Also, the microspheres 22 can be round, spherical, and symmetrical, or they can be irregular, rough, jagged, or nonsymmetrical. The microspheres 22 are then contained within the matrix 20. As such, the microspheres 22 can elute from the pore 16, and/or the active agent can diffuse out of the microspheres 22 which are retained within the pore 16. For example, the microspheres 22 can elute from the pore 16 in the case of a biodegradable matrix 20, where the active agent 18 diffuses from the microspheres 22. Alternatively, the active agent 18 can diffuse from the microsphere 22 while disposed within the pore 16, through the matrix 20, and then elute from the pore 16. Additionally, other similar configurations that include the use of microspheres 22 can be used.

Portion C is similar to Portion A in that it shows that the active agent 18 can be deposed into a pore 16 and then covered with matrix 20, which forms a protective barrier for the active agent. However, the matrix 20 is disposed within the pore 16 in a manner such that a portion of the matrix 20 does not protrude out of the pore 16, and the matrix 20 is protected by the porous body 14.

Portion D shows a first active agent composition 24 and a second active agent composition 26 disposed within the pore 16. More particularly, the first active agent composition 24 is shown to be disposed at the bottom of the pore 16 and covered with a layer of the matrix 20, which in turn is covered with the second active agent composition 26 that is covered with another layer of the matrix 20. Such a configuration can be useful when the first active agent composition 24 and second active agent composition 26 have different active agents or different formulations. Also, the two different matrix 20 layers can have the same composition or different compositions so as to alter the rate of elution of the active agent from the pore 16. For example, the active agent in the second active agent composition 26 can be useful for a first stage of a therapy and the active agent in the first active agent composition 24 can be useful for a second stage of a therapy. In another example, the active agent in the first active agent composition 24 may diffuse through the matrix 20 at a faster rate, and thereby elute from the pore 16 concomitantly. Also, the outer matrix 20 can be substantially more resilient to forces than the inner matrix 20, and thereby the outer matrix 20 can provide protection to the inner matrix 20 and the active agent compositions 24, 26). Additionally, other similar configurations that include the use of multiple active agent compositions can be used.

Portion E is similar to Portion B in that it shows a first microsphere 28 and a second microsphere 30 disposed within the pore 16. The microspheres 28, 30 are then contained within the matrix 20, and a topcoat 32 is applied over the matrix 20 to protect the matrix 20 and microspheres 28, 30 from mechanical damage. As such, the microspheres 28, 30 can elute from the pore 16 as described in connection with Portion B. Also, the microspheres 28, 30 can have different formulations as described in connection with Portion D. Additionally, other similar configurations that include the use of different microsphere 28, 30 formulations can be used.

In any of the portions A-E, the active agent composition can include an elution rate controlling matrix. As such, multiple elution rate controlling matrices can be used. Alternatively, only a single elution rate controlling matrix containing the active agent can be used.

Figure 2:
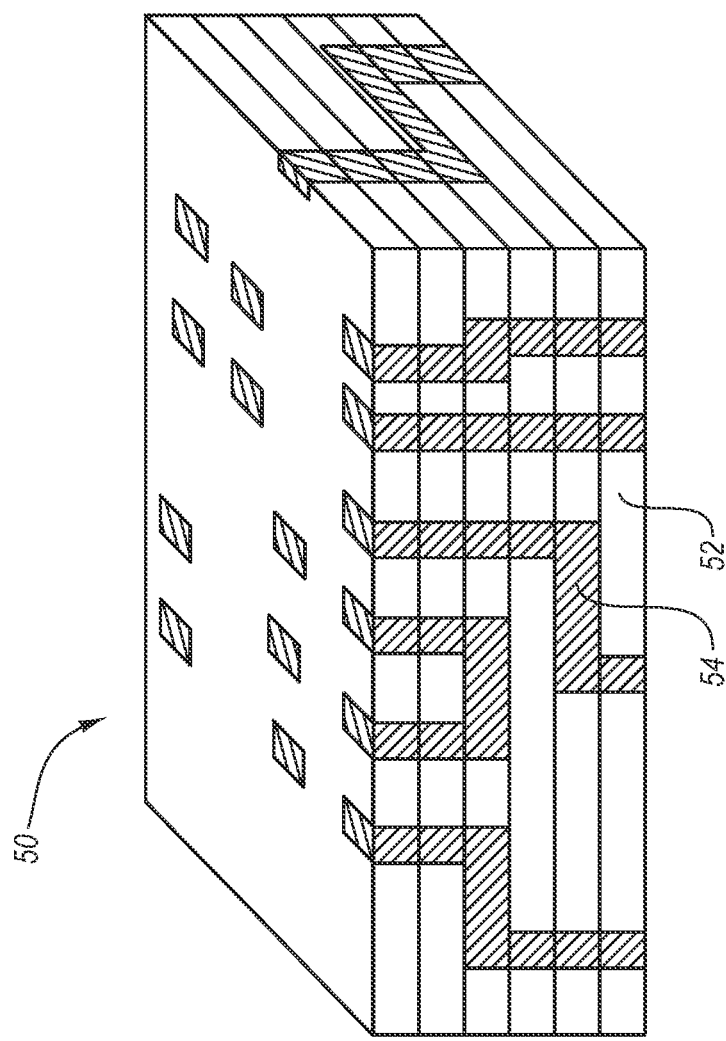
FIG. 2 is a cross-sectional view illustrating an embodiment of a porous body having a plurality of pores.

FIG. 2 is a schematic representation of a portion of an embodiment of a porous body 50 in accordance with the present invention. The porous body 50 is comprised of a plurality of layers 52 that are configured and dimensioned such that the consecutive layers 52 form a plurality of pores 54. Such a porous body 50 can be prepared layer-by-layer in a manner that results in a plurality of pores. Exemplary methods of preparing such a porous body 50 comprised of a plurality of layers 52 can include direct rapid prototyping, metal printing processes, and the like, which are described in more detail below.

In one embodiment, the elution rate controlling matrix can include a combination or mixture of a non-polymeric material and a polymeric material.

In one embodiment, the elution rate controlling matrix can include the active agent and radiopaque dyes or particles.

In one embodiment, the medical device can include a topcoat that covers the pores of the porous body. Alternatively, the topcoat can be applied onto the matrix in order to provide additional protection or to confer desirable controlled release characteristics. As such, the topcoat can be configured to include various functions, such as the following: it can provide a smooth outer profile for the porous body; it can minimize loss of the active agent during delivery; it can provide a biocompatible interface with tissue (e.g., blood vessel) after implantation; and it can aide in controlling the release of the active agent from the pores into the surrounding tissue or body fluid upon use. The topcoat may include, or be substantially free of, any active agents. In some instances, the topcoat is applied over the porous body. In other instances, the top coat is disposed substantially within the pores such that the top coat does not protrude from the pores. In other instances, the topcoat is at least partially included in the pores such that the topcoat is anchored into the pore complex. Thus, the adhesion of the topcoat to the surface of the device is improved or even largely achieved by its anchoring into the pores.

A. Exemplary Medical Devices

In one embodiment, the medical device can be an endoprosthesis, such as an endovascular and/or intracoronary device. Examples include drug delivery catheters, grafts, drug delivery balloons, guidewires, stents, filters, grafts, valves, occlusive devices, trocars, aneurysm treatment devices, and accessories used in vascular intervention. Additionally, an endoprosthesis can be configured for a variety of intralumenal applications, including vascular, coronary, biliary, esophageal, urological, gastrointestinal, nasal, or the like. When the medical device is an endoprosthesis, multiple configurations of endoprostheses may be utilized including, but not limited to, peripheral endoprostheses, peripheral coronary endoprostheses, degradable coronary endoprostheses, non-degradable coronary endoprostheses, self-expanding endoprostheses, balloon-expanded endoprostheses, and esophageal endoprostheses. However, the drug eluting endoprostheses of the invention may be manufactured into a number of different configurations. These medical devices may have a primary function that is different from the release of the drug. For example, an endoprosthesis may be primarily used for maintaining the patency of a lumen, and also releases a drug to prevent restenosis of a lumen. The medical device may have drug delivery as its primary function, for instance an implantable system for the local delivery of a therapeutic substance like an anti-cancer drug.

In one embodiment, the medical devices include an implant indwelling device. Examples include orthopedic implants, ocular implants, pharmacotherapeutic implants, dental implants, other prosthetic implants, fixation screws, indwelling catheters, any other indwelling device, and other implant or indwelling medical devices that are deployed so as to be in contact with bodily fluid or tissue.

In one embodiment, the medical device includes blood-contacting components of extracorporeal devices. Thus, the medical device configured in accordance with the present invention can be a portion of an extracorporeal device that comes into contact with a body part of a body fluid. For example, the medical device can be a portion of a kidney dialysis system that contacts the body fluid.

In one embodiment, the medical device includes a surgical or medical procedure tool. Examples can include staples, filters, needles, tubes, coils, wires, clips, screws, sensors, plates, conduits, and the like. In fact, the medical device can be any medical tool that is used in a medical procedure in a manner that would allow for the drug to be eluted from the device so as to provide a beneficial function.

In one embodiment, the medical device can have a delivery orientation and a deployed orientation. For example, a stent has a delivery orientation that has a much narrower cross-sectional profile compared to the deployed orientation. This allows the stent in the delivery orientation to be delivered through the tortuous vasculature pathway before being expanded into the deployed orientation that provides structural support to the vasculature.

B. Medical Device Compositions

The supporting structure and/or porous body of the medical devices of the present invention can be made of a variety of materials, such as, but not limited to, those materials which are well known in the art of medical device manufacturing. As such, the supporting structure and/or porous body can be prepared from the same materials or different materials. Generally, the materials for the supporting structure and/or porous body can be selected according to the structural performance and biological characteristics that are desired. Materials well known in the art for preparing medical devices (e.g., endoprostheses), such as polymers, ceramics, and metals, can be employed in preparing the supporting structure and/or porous body.

In one embodiment, the medical device can include a material made from any of a variety of known suitable materials, such as a shaped memory material ("SMM") or superelastic material. For example, the SMM can be shaped in a manner that allows for restriction to induce a substantially tubular, linear orientation while within a delivery shaft (e.g., delivery catheter), but can automatically retain the memory shape of the medical device once extended from the delivery shaft. SMMs have a shape memory effect in which they can be made to remember a particular shape. Once a shape has been remembered, the SMM may be bent out of shape or deformed and then returned to its original shape by unloading from strain or heating. SMMs can be shape memory alloys ("SMA") or superelastic metals comprised of metal alloys, or shape memory plastics ("SMP") comprised of polymers.

An SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium ("NiTi") alloys known as nitinol; and cobalt-chromium-nickel alloys or cobalt-chromium-nickel-molybdenum alloys known as elgiloy. The nitinol and elgiloy alloys can be more expensive, but have superior mechanical characteristics in comparison with the copper-based SMAs. The temperatures at which the SMA changes its crystallographic structure are characteristic of the alloy, and can be tuned by varying the elemental ratios.

For example, the primary material of the supporting structure and/or porous body can be of a NiTi alloy that forms superelastic nitinol. Nitinol materials can be trained to remember a certain shape, straightened in a shaft, catheter, or other tube, and then released from the catheter or tube to return to its trained shape. Also, additional materials can be added to the nitinol depending on the desired characteristic.

An SMP is a shape-shifting plastic that can be fashioned into the supporting structure and/or porous body in accordance with the present invention. When an SMP encounters a temperature above the lowest melting point of the individual polymers, the blend makes a transition to a rubbery state. The elastic modulus can change more than two orders of magnitude across the transition temperature ("$T_{tr}$"). As such, an SMP can be formed into a desired shape of the supporting structure and/or porous body by heating it above the $T_{tr}$, fixing the SMP into the new shape, and cooling the material below $T_{tr}$. The SMP can then be arranged into a temporary shape by force and then resume the memory shape once the force has been applied. Examples of SMPs include, but are not limited to, biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

Also, it can be beneficial to include at least one layer of an SMA and at least one layer of an SMP to form a multilayered body; however, any appropriate combination of materials can be used to form a multilayered medical device.

The supporting structure and/or porous body can be comprised of a variety of known suitable deformable materials, including stainless steel, silver, platinum, tantalum, palladium, cobalt-chromium alloys such as L605, MP35N, or MP20N, niobium, iridium, any equivalents thereof, alloys thereof, and combinations thereof. The alloy L605 is understood to be a trade name for an alloy available from UTI Corporation of Collegeville, Pa., including about 53% cobalt, 20% chromium and 10% nickel. The alloys MP35N and MP20N are understood to be trade names for alloys of cobalt, nickel, chromium and molybdenum available from Standard Press Steel Co., Jenkintown, Pa. More particularly, MP35N generally includes about 35% cobalt, 35% nickel, 20% chromium, and 10% molybdenum, and MP20N generally includes about 50% cobalt, 20% nickel, 20% chromium and 10% molybdenum.

Also, the supporting structure and/or porous body can include a suitable biocompatible polymer in addition to or in place of a suitable metal. The polymeric supporting structure and/or porous body can include a biocompatible material, such as biostable, biodegradable, or bioabsorbable materials, which can be either plastically deformable or capable of being set in the deployed configuration. If plastically deformable, the material can be selected to allow the medical device (e.g., stent) to be expanded in a similar manner using an expandable member so as to have sufficient radial strength and scaffolding and also to minimize recoil once expanded. If the polymer is to be set in the deployed configuration, the expandable member can be provided with a heat source or infusion ports to provide the required catalyst to set or cure the polymer. Biocompatible polymers are well known in the art, and examples are recited with respect to the polymeric matrix. Thus, the matrix, supporting structure, and/or porous body can be prepared from a biocompatible polymer.

Furthermore, the supporting structure and/or porous body can be formed from a ceramic material. In one aspect, the ceramic can be a biocompatible ceramic. Examples of suitable ceramic materials include bioinert ceramic, alumina, surface-bioactive ceramics, silicon carbide, zirconia, hydroxyapatite (HA), bioglasses, resorbable bioactive ceramics, alpha and/or beta tricalcium phosphates (TCP), tetracalcium phosphate (TTCP), octacalcium phosphate, calcium sulfate, dicalcium phosphate dihydrate (DCPD), hydrated calcium phosphates, calcium hydrogen phosphate, dicalcium phosphate anhydrous (DCPA), low-crystallinity HA, calcium pyrophosphates (anhydrous or hydrated), calcium polyphosphates ($n \geq 3$), calcium polyphosphate, calcium silicates, calcium carbonate, amorphous calcium salts, whitlockite, zeolites, artificial apatite, brushite, calcite, gypsum, phosphate calcium ore, iron oxides, calcium sulphate, magnesium phosphate, calcium deficient apatites, amorphous calcium phosphates, and combinations thereof. Various ceramics can be crystalline, amorphous, glassy, anhydrous, or hydrated. Ceramics generally contain one or more of titanium, zinc, aluminium, zirconium, magnesium, potassium, calcium, iron, ammonium, and sodium ions or atoms in addition to one or more of an oxide, a phosphate (ortho, pyro, tri, tetra, penta, meta, poly etc), a silicate, a carbonate, a nitride, a carbide, a sulphate, ions thereof, or the like. Also, other materials with similar properties that can be fabricated into a ceramic as described herein can be included in the present invention.

Preferred ceramics include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like.

Moreover, the supporting structure and/or porous body can include a radiopaque material to increase visibility during placement. Optionally, the radiopaque material can be a layer or coating any portion of the supporting structure and/or porous body. The radiopaque materials can be platinum, tungsten, silver, stainless steel, gold, tantalum, bismuth, barium sulfate, or a similar material.

In one embodiment, the medical device in the form of a stent or other tubular medical device can be comprised of a shape-memory material, where an outer sheath may be disposed over the medical device to confine the medical device in a contracted state, while retraction of the outer sheath causes the medical device to self-expand to a deployed shape.

The elution rate controlling matrix can be prepared with at least one polymeric material having the properties of being biocompatible, bioabsorbable, biodegradable, bioerodible, naturally occurring, synthetic, or any combination thereof. Such a polymeric material can include at least one natural or synthetic, homopolymer or copolymer (without limitation to the amount of different monomers), linear, branched or cross-linked, soluble or insoluble, biostable or biodegradable, hydrophilic, hydrophobic, intermediate or amphiphilic, neutral or ionically charged, or polymerized with pendant groups. The polymers can include condensation and addition polymers, macromolecules, thermoplastic elastomers, polyolefin elastomers, biostable plastics, and the like.

In one embodiment, the polymeric material can include phosphorylcholines, phosphorylcholine linked macromolecules, polyolefins, poly(meth)acrylates, polyurethanes, polyesters, polyanhydrides, polyphosphazenes, polyacrylates, acrylic polymers, pendant phosphoryl groups, poly(lactide-co-glycolide) (PLGA), polycaprolactones, polylactic acids (PLA), poly(hydroxybutyrate), poly(hydroxybutyrate-co-valerate), polydioxanone (PDO), polyorthoester, polyglycolic acid (PGA), polycaprolactone (PCL), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyiminocarbonates, aliphatic polycarbonates, fibrin, fibrinogen, cellulose, starch, collagen, Parylene®, Parylast®, polycarbonate urethanes, polyisoprene, polyisobutylene, polybutadiene, polyethylene, plasticized polyethylene terephthalate, polyethylene terepthalate, polymethylmethacrylate, ethylene ethylacrylate, polyethyl hexylacrylate, plasticized ethylene vinylacetate, polyvinyl acetate, ethylene vinyl acetate, ethylene vinyl alcohol, polyvinyl alcohol, cross-linked polyvinyl alcohol, cross-linked polyvinyl butyrate, polyvinylbutyrate, polybutylmethacrylate, polyvinyl chloride, ethylene vinylchloride copolymer, silicones, polysiloxanes, substituted polysiloxanes, polyethylene oxide, polyethylene glycol (PEG), polybutylene terepthalate-co-PEG, PCL-co-PEG, PLA-co-PEG, polyvinyl acetals, polyvinyl acetates, polyvinyl formal, polyamides, polyvinyl pyrrolidone, polyacrylamide, polyvinyl esters, copolymers thereof, polymer derivatives thereof, and combinations thereof. Also, the polymer can be poly($MPC_w$:$LMA_x$:$UPMA_y$:$TSMA_z$), where MPC is 2-methacryoyloxyethylphosphorylcholine, LMA is lauryl methacrylate, HPMA is hydroxypropyl methacrylate and TSMA is trimethoxysilylpropyl methacrylate, In one embodiment, the elution rate controlling matrix is a biodegradable polymer selected from the group consisting of poly(L-lactic acids), poly(DL-lactic acids), polycaprolactones, polyhydroxybutyrates, polyglycolides, poly(diaxanones), poly(hydroxy valerates), polyorthoesters, poly(lactide-co-glycolides), polyhydroxy(butyrate-co-valerates), polyglycolide-co-trimethylene carbonates, polyanhydrides, polyphosphoesters, polyphosphoester-urethanes, polyamino acids, polycyanoacrylates, biomolecules, fibrin, fibrinogen, cellulose, starch, collagen, hyaluronic acid, mixtures thereof, derivatives thereof, copolymers thereof, and like polymers.

In one embodiment, the elution rate controlling matrix is a biostable polymer selected from the group consisting of polyurethanes, silicones, polyesters, polyolefins, polyamides, polycaprolactams, polyimides, polyvinyl chlorides, polyvinyl methyl ethers, polyvinyl alcohols, acrylic polymers, polyacrylonitriles, polystyrenes, vinyl polymers, polymers including olefins (e.g., styrene acrylonitrile copolymers, ethylene methyl methacrylate copolymers, ethylene vinyl acetate, and other like polymers), polyethers, rayons, cellulosics (e.g., cellulose acetate, cellulose nitrate, cellulose propionate, and other like polymers), parylene, mixtures thereof, derivatives thereof, copolymers thereof, and like polymers.

In one embodiment, the elution rate controlling matrix includes a non-polymeric material such as sugars, waxes, and lipids.

Additionally, the elution rate controlling matrix can be formulated with a pharmaceutically acceptable carrier, which is a non-toxic solid, semi-solid or liquid filler, diluent, encapsulating material or formulation auxiliary of any type. The compositions that can be included can be comprised of pharmaceutically acceptable sterile aqueous or nonaqueous solutions, dispersions, suspensions or emulsions, as well as sterile powders for reconstitution into sterile solutions or dispersions just prior to be included with the endoprosthesis. Examples of suitable aqueous and nonaqueous carriers, diluents, solvents, or vehicles include water, ethanol, polyols (e.g., glycerol, propylene glycol, polyethylene glycol, and the like), carboxymethylcellulose and suitable mixtures thereof, vegetable oils (e.g., olive oil), organic esters such as ethyl oleate, and the like.

The elution rate controlling matrix may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminum monostearate and gelatin.

In some cases, in order to prolong the effect of the drug, it is desirable to slow the release of the drug from the elution rate controlling matrix. This may be accomplished by the use of crystalline or amorphous materials with poor water solubility. The rate of absorption of the drug can depend upon its rate of dissolution which, in turn, may depend upon crystal size and crystalline form. Alternatively, delayed release can be accomplished by dissolving or suspending the drug in an oil or hydrophobic carrier prior to being included with the elution rate controlling matrix.

Additionally, the elution rate controlling matrix can be formulated to be or to include microencapsule matrices, such as microspheres, before being included with the medical device. Similarly, the elution rate controlling matrix can include in liposomes, microspheres, microparticles, microemulsions, or the like that contain the active agent.

The elution rate controlling matrix can also include other pharmaceutically acceptable materials, such as any of the following: excipients or carriers such as sodium citrate or dicalcium phosphate; fillers or extenders such as starches, lactose, sucrose, glucose, and mannitol; binders such as, for example, carboxymethylcellulose, alginates, gelatin, polyvinylpyrrolidone, sucrose, and acacia; humectants such as glycerol; disintegrating agents such as agar, calcium carbonate, starch, alginic acid, certain silicates, and sodium carbonate; solution retarding agents such as paraffin; absorption accelerators such as quaternary ammonium compounds; wetting agents such as cetyl alcohol and glycerol monostearate; absorbents such as kaolin and bentonite clay; and lubricants such as talc, calcium stearate, magnesium stearate, solid polyethylene glycols, and sodium lauryl sulfate.

In one embodiment the porous material of the applied layer includes at least one of biocompatible metals, metal alloys, ceramics, and polymers. Metals include, but are not limited to, pure metals, such as gold or tantalum, metal compositions such as stainless steel, or alloys such as cobalt chromium.

C. Active Agents

The active agents of the present invention can include any substance that has a biological activity, such as pharmacological agents. Such active agents include analgesics, antipyretics, antiasthamatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, and combinations thereof. Alternatively, the compounds or agents would be in the form of components of molecular complexes or pharmacologically acceptable salts.

In one embodiment, the active agent includes at least one of zotarolimus, sirolimus, everolimus, dexamethasone, prednisone, hydrocortisone, estradiol, acetaminophen, ibuprofen, naproxen, sulidac, heparin, taxol, paclitaxel, and any combination thereof.

In one embodiment, the active agents can be anti-restenosis agents, such as anti-proliferative agents, anti-platelet agents, anti-inflammatory agents, anti-thrombotic agents, and thrombolytic agents. The anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include vincristine, paclitaxel, etoposide, nocodazole, indirubin, anthracycline derivatives, daunorubicin, daunomycin, plicamycin, and the like. Other sub-classes of anti-mitotic agents include anti-mitotic alkylating agents, such as, for example, tauromustine, bofumustine, and fotemustine, and anti-mitotic metabolites, such as methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v\beta 3$, antibodies that block binding to gpIIaIIIb or $\alpha v\beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

The active agent can also be an immunosuppressant agent. The immunosuppressant agents can include azathioprine sodium, brequinar sodium, gusperimus trihydrochloride (also known as deoxyspergualin), mizoribine (also known as bredinin), mycophenolate mofetil, cylosporin A, tacrolimus (also known as FK-506), sirolimus, leflunomide (also known as HWA-486), glucocorticoids such as prednisolone and its derivatives, antibody therapies such as orthoclone (OKT3), and antithymyocyte globulins, such as thymoglobulins.

III. Method of Manufacture

Various different manufacturing techniques are well known and may be used for fabrication of the medical devices of the present invention. For example, and in a preferred embodiment, the medical device is manufactured into an endoprosthesis, such as a stent. As such, the supporting structure and/or porous body in accordance with the present invention can be prepared as described below with respect to the endoprosthesis. That is, references to endoprostheses are intended to broadly encompass the medical devices of the present invention.

In one embodiment, the present invention includes a method of manufacturing a medical device used for treating and/or preventing a disease in an animal. Such a method can include the following: fabricating a supporting structure, which can include shaping the supporting structure into the medical device, such as an endoprosthesis (e.g., stent); fabricating a porous body onto at least a portion of the supporting structure, said porous body including a first biocompatible material having a plurality of pores; introducing a therapeutically effective amount of an active agent into at least a portion of the pores, said therapeutically effective amount of the active agent being capable of treating and/or preventing a disease; and introducing an elution rate controlling matrix onto at least one surface of the porous body so as to contain the active agent within said at least a portion of the pores, said matrix including a second biocompatible material that controls the elution of the active agent from the pores.

In one embodiment, the fabrication of the porous body can include dimensioning and configuring the porous body to have a thickness ranging from about 10 nanometers to about 1 millimeter. Also, the fabrication of the porous body can include dimensioning and configuring the pores to have a diameter of from about 10 nanometers to about 1 millimeter.

In one embodiment, the method of manufacture can include configuring the medical device to be at least one of an endoprosthesis, drug delivery stent, drug delivery catheter, graft, drug delivery balloon, guidewire, orthopedic implant, dental implant, fixation screws, indwelling catheter, ocular implant, pharmacotherapeutic implant, blood-contacting component of extracorporeal device, staple, filter, needle, tube, coil, wire, clip, screw, sensor, plate, conduit, portion thereof, or combination thereof.

In one embodiment, the method of manufacture can include combining the active agent with the elution rate controlling matrix. This can include combining the active agent and elution rate controlling matrix before, during, or after being introduced into the porous body. As such, the active agent can be absorbed into the elution rate controlling matrix after being introduced into the porous body.

In one embodiment, the method of manufacture can include any of the following processes, which are provided as examples without limitation: fabricating the supporting structure and/or porous body by sintering; fabricating the supporting structure and/or porous body by a metal printing process; fabricating the supporting structure and/or porous body by a direct rapid prototyping process; shaping the porous structure from a mixture of two components, one of which is leached out after the shaping process, leaving the other, permanent component in a porous form; freeze-drying or other similar process where a solid is removed by sublimation from a phase separated mixture of two or more components; by a process similar to supercritical fluid evaporation or foaming; and/or shaping the supporting structure and/or porous body into an endoprosthesis, such as a stent.

In one embodiment, the method of manufacture includes configuring the pores of a porous layer disposed upon the endoprosthesis to accommodate at least one elution rate controlling material and at least one agent. Through configuring the size of the orifice, volume and shape of the pores, as well as the amount of elution rate controlling material and agent, the pores are manufactured to control or determine the rate of elution of an agent. The configured shapes and sizes of the pores within the porous material of the invention depend on many variables including, but not limited to: the amount of drug delivery needed, elution rates of the material and how the elution rate controlling material is dispersed, (e.g., encapsulated, co-incorporated, or co-encapsulated, or associated) with the agents; treatment and/or prevention of a particular disease; the agents utilized; the type of medical device and its interactions with other medical devices; the position and location of the medical device in the animal body and body (including tissue and fluid) interactions; and combinations of positions and interactions between the body and medical device.

In one embodiment, the medical device can be shaped into an endoprosthesis, (e.g., stent) which can be formed from a hollow tube of suitable material using a known technique, such as by laser cutting, EDM, milling, chemical etching, hydro-cutting, and the like. The shaped structure can be mechanically blasted with a media and then electropolished or otherwise finished to remove burrs and eliminate sharp edges and contaminates. An additional de-scaling process may be performed before electropolishing, wherein the de-scaling process involves the use of an acid bath.

Alternatively, a stent body can be fabricated from a sheet of suitable material using a similar cutting, milling, or etching technique, and then rolled or bent about a longitudinal axis into the desired shape. If desired, the lateral edges of the structure can be joined together, such as by welding or bonding, to form a closed tubular structure, or the lateral edges can remain unattached to form a coiled, rolled sheet or open tubular structure.

An additional step of passivation can be performed during the manufacturing stage of the endoprosthesis in order to form a homogeneous oxide layer for corrosion resistance. The passivation process may be performed prior to installation of the markers in accordance with the present invention or it may be performed after installation of radiopaque markers. Alternatively, multiple passivation processes may be performed prior to insertion of the markers and again after insertion of the markers.

A. Shaping and Pore Formation

Accordingly, a medical device, such as an endoprosthetic material can be shaped by various methods as described in more detail below. Such shaping techniques can utilize streams of energy and/or streams of matter in order to impart shapes and/or pores into the endoprosthetic material. The streams of energy include photons, electromagnetic radiation, atomic, and sub-atomic materials, as described above. On the other hand, the streams of matter are considered to include materials larger than atomic scale particles, and can be microscopic or macroscopic in size. In any event, the shaping can be designed to direct a stream of energy or a stream of matter at the endoprosthetic material to form an endoprosthetic material and/or pores therein. Also, mechanical drills can be used to drill pores into an endoprosthesis.

In one embodiment, a stream of energy can cut, shape, and/or form pores in the endoprosthetic material by generating heat at the site where the stream intersects the material, as is well known in the art. The thermal interaction can elevate the local temperature to a point which can cut, melt, shape, and/or vaporize portions of the endoprosthetic material from the rest of the material. Accordingly, one embodiment of the stream-cutting apparatus can operate and shape the endoprosthetic material by thermal interactions. As such, any of the thermal processes described herein can be used for thermal-cutting. For example, such thermal interactions can arise from laser beam treatment, laser beam machining, electron beam machining, electrical discharge machining, ion beam machining, and plasma beam machining.

In one embodiment, by knowing the thermal properties of the endoprosthetic material, precise energy requirements can be calculated so that the thermal beam provides the appropriate or minimum energy for melting and/or vaporizing the material without significantly melting undesirable portions of the material. For example, laser beams are a common form of a stream of energy that can be used to shape or form pores in the endoprosthetic material. Additionally, there are instances where a laser is preferred over all other cutting techniques because of the nature of the resulting endoprosthesis as well as the characteristics of the endoprosthetic material.

Accordingly, a laser can cut the endoprosthetic material and/or form pores therein, wherein the power of the laser or the heat generated can depend upon the composition of the material to be cut. The ability to vary the laser power arises due to the use of different materials or vary the thickness of the same. The laser power can be defined as the rate of which energy is delivered by the beam and is usually measured in units as joules/second or watts. For example, lasers typically used in cutting hardened steel, such as YAG or eximer lasers, can have a power of about 2,000 watts or greater. Some endoprosthetic materials can be shaped with lasers operating below about 2,000 watts, more preferably below about 1,000 watts, and most preferably below about 500 watts. In one configuration, a femto-second laser can be used to shape the material, optionally including forming pores therein. Use of the femto-second laser also reduces the heated affected zone (HAZ) of the material during manufacturing. Reducing the localized thermal stress upon the material.

In one embodiment, electrical discharge machining can be used to shape endoprosthetic material and/or form the pores therein. As such, electrical discharge machining is capable of cutting all types of conductive materials such as exotic metals (e.g., titanium, hastaloy, kovar, inconel, hard steels, carbides, and the like). In electrical discharge, the main interaction between the stream of energy and the endoprosthetic material is thermal, where heat is generated by producing electrical discharges. This can lead to the endoprosthetic material being removed by melting and evaporation. Some examples of electrical discharge machining include wire electron discharge machining, CNC-controlled electrical discharge machining, sinker electrical discharge machining, small hole discharge machining, and the like.

In another embodiment, a charged particle beam can be used for shaping and/or forming pores in the endoprosthetic material, wherein charged particle beams are exemplified by electron beams and ion beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams can be useful for cutting and shaping of the endoprosthetic material, as described herein. Additionally, there are some instances where electron beams or ion beams are preferred over other cutting techniques.

In one embodiment, a stream of chemical matter can be used in order to shape and/or form pores in the endoprosthetic material such as chemical etching or chemical-jet milling. Chemical-jet milling, for example, provides selective and controlled material removal by jet and chemical action. As such, the process is similar to water-jet cutting, which is described in more detail below. In any event, chemical-jet milling can be useful for shaping or forming pores in various types of endoprosthetic materials, which provides intricate shaping capabilities.

In another embodiment, electrochemical shaping and/or pore formation can be used, and is based on a controlled electrochemical dissolution process similar to chemical-jet milling an endoprosthetic material. As such, the endoprosthetic material can be attached to an electrical source in order to allow an electrical current to assist in the shaping and/or pore formation.

In one embodiment, hydro-cutting or water-jet cutting can be used to shape and/or form pores in an endoprosthetic material. Hydro-cutting is essentially a water-jet technology that uses the high force and high pressure of a stream of water directed at the endoprosthetic material in order to cut and shape the material as desired. Hydro-cutting can be preferred over some of the other stream-cutting technologies because it can be free of heat, flame, and chemical reactions, and can provide a precise cold shaping technique. Also, heated water with or without being doped with reactive chemicals can also be used. Hydro-cutting is particularly suitable for a polymeric endoprosthesis, but can be used for some metal materials when combined with abrasive particles, as described below.

Additionally, hydro-cutting can be enhanced by the introduction of particulate materials into the water feed line. As such, some hydro-cutting techniques utilize garnet or other rigid and strong materials in order to apply an abrasive cutting force along with the force applied by the water itself.

In one embodiment, sandblasting, which fits into the regime of stream of matter cutting, can be used to shape and/or form pores in an endoprosthetic material by projecting a high energy stream of sand particles at the material. Sandblasting cuts materials similar to hydro-cutting, especially when the water-jet is doped with abrasive particulates. Additionally, various other particulate streams other than sand can be used in the stream-cutting techniques and machinery.

B. Sintering

In one embodiment, a method of making a supporting structure and/or porous body in accordance with the present invention can include sintering sinterable particles to provide a sintered article having the shape of the medical device, such as an endoprosthesis. Briefly, the sintered body can be obtained from a green body prepared by molding a mixture of sinterable particles with or without a binder into the shape of an endoprosthesis or body intermediate. The molded green body may have the shape of the endoprosthesis with or without pores. After the green body has been formed in the mold and sintered into a hardened endoprosthesis, the process can include shaping the sintered body with a stream of energy and/or matter in order to obtain a desired shape. In any event, sintering a green body in a mold can result in an endoprosthesis that is either ready for use, or requires additional processing or finishing such as shaping and/or pore forming.

In one embodiment, a de-binding process can be carried out to remove the binder prior to sintering the green body. As such, the de-binding can be performed by heat treatment in an oxidizing or non-oxidizing atmosphere, for instance, under a vacuum or low pressure. Such debinding can be utilized in order to form pores in the finished product.

When the green body is sintered, the volume can either shrink as the porosity decreases and the density increases or stay roughly the same with an increase in porosity. This is especially true when the sinterable particles are held together with a binder and can happen as the majority of the binder is melting and/or evaporating so as to draw the individual sinterable particles closer together or create voids between particles. As such, the green body can be fabricated, molded, and/or shaped to be larger than the resultant sintered article in order to accommodate for the volume lost or pore enlargement during sintering.

Accordingly, the sintered body can be shaped into a supporting structure and/or porous body with pores as described herein. Also, the endoprosthesis can be further processed after sintering and/or shaping such as by grinding, sanding, or the like to provide enhanced surface characteristics.

Further, the method can include depositing the elution rate controlling material, such as a biodegradable material or a material impregnated with an active agent, onto the pores. The deposited material can partially or substantially fill the pores.

C. Direct Rapid Prototyping

Additionally, the medical devices of the present invention can be prepared using a direct rapid prototyping system and process to manufacture the supporting structure and/or porous body. This can include a system and process that employs the direct rapid prototyping system and process to print the metal and/or ceramic to form the supporting structure and/or porous body.

In one embodiment, the system and process for preparing the supporting structure and/or porous body can include direct three-dimensional (3D) printing. Direct 3D powder printing can be used for rapid prototyping or r large-scale manufacturing. As such, the supporting structure and/or porous body can be custom made or prepared in an assembly line manner. Rapid prototyping commonly refers to a class of technologies that can automatically construct physical models in 3D from Computer-Aided Design (CAD) files. Rapid prototyping machines can be considered to be three dimensional printers that allow for prototypes or functional products to be quickly created and manufactured. In addition to prototypes, rapid prototyping systems and processes can also be used to make production-quality objects and is sometimes referred to as rapid manufacturing. For small production runs and complicated objects, rapid prototyping can be advantageous over other manufacturing processes. This is especially true given that the systems and processes can be modulated to account for various temperatures, pressures, or other processing limitations that may be imposed by a particular product or reagent (e.g., temperature sensitive bioactive substance). While the process is relatively fast, some supporting structure and/or porous body may require from three to seventy-two hours to build, depending on the size and complexity of the medical device.

In order to design a supporting structure and/or porous body, a software package virtually-slices a CAD model into a number of thin (about 100 microns) layers so that the direct inkjet printing component can then built up one layer atop another in order to form the endoprosthesis. As such, direct inkjet printing is an additive process that combines successive layers of ceramic and/or bioactive substance to create a solid endoprosthesis. Generally, direct inkjet printing can include the following steps: create a CAD model of the design using a computing system; convert the CAD model to STL format or other appropriate format using the computing system; slice the STL file into virtual thin cross-sectional layers using the computing system; physically construct the model one layer atop another layer by sequentially inkjet printing each layer in successive steps; and clean and finish the endoprosthesis.

Figure 3:
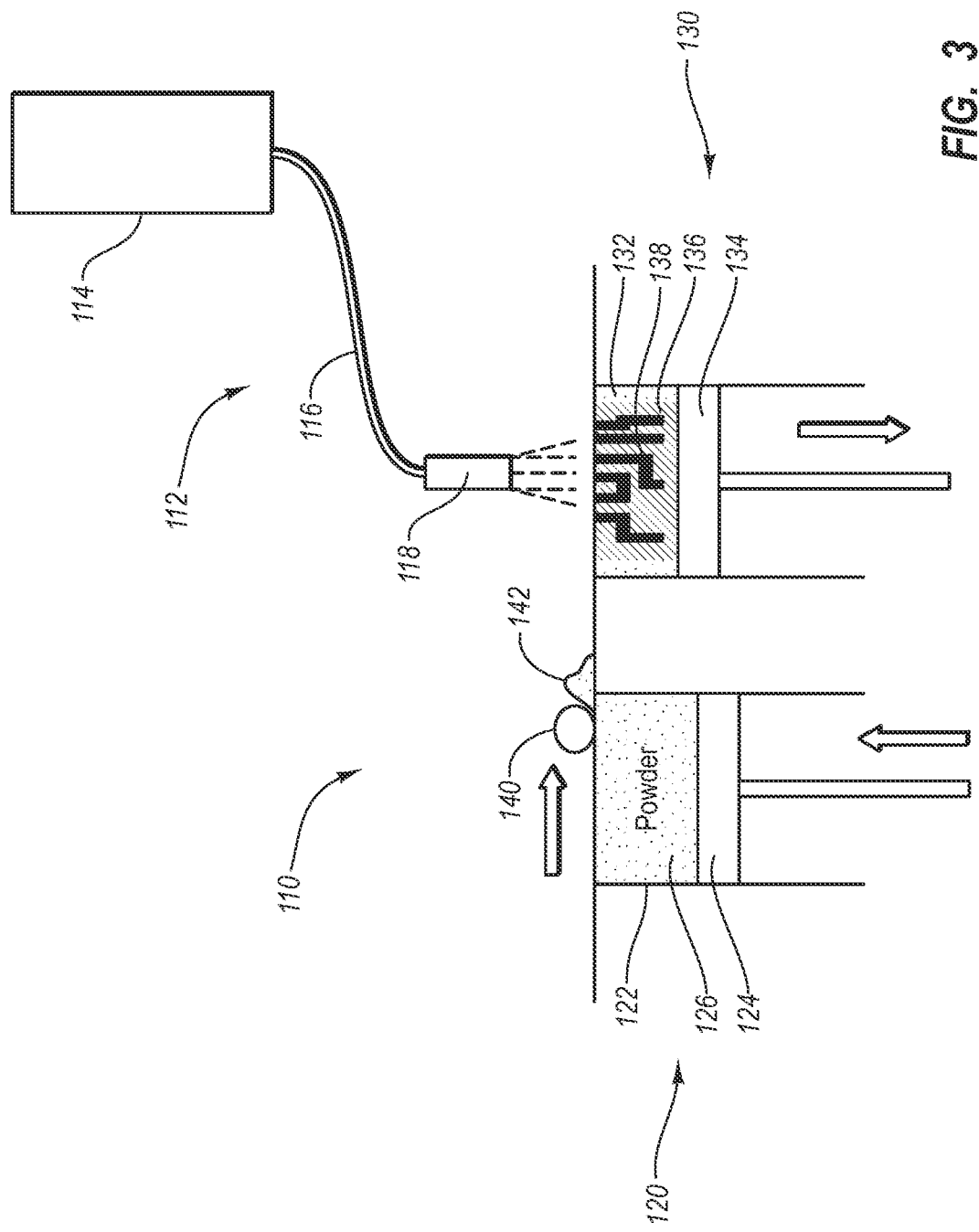
FIG. 3 is a schematic representation of an embodiment of a direct rapid prototyping process for preparing a medical device in accordance with the present invention.

FIG. 3 illustrates an embodiment of a direct rapid prototyping inkjet printing system and process for using inkjet technologies in order to prepare a supporting structure and/or porous body (i.e., endoprosthesis). Generally, direct rapid prototyping inkjet systems and methods that are well known in the art can be configured to operate under the present invention. Optionally, direct rapid prototyping systems and processes can be configured to eliminate a sintering step or other step that causes excessive heat and/or pressure. Otherwise, the endprosthesis prepared by direct rapid prototyping can be sintered as is well known in the art. As used herein, direct inkjet printing refers to an entire class of machines that employ inkjet technology to sequentially build an endoprosthesis layer-by-layer. An example of such a direct inkjet printer capable of operating under the present invention is a ZCorp 3D printer, produced by Z Corporation of Burlington, Mass.

FIG. 3 depicts an embodiment of a direct inkjet printing system 110 and process in accordance with the present invention. The direct inkjet printing system 110 includes an inkjet printer 112, a powder delivery system 120, a roller 140, and a fabrication system 130.

The inkjet printer 112 has at least one inkjet cartridge 114 that can include any composition capable of being inkjet printed. Additionally, the inkjet printer 112 includes an inkjet line 116 that routes the inkjet composition from the inkjet reservoir 114 to an inkjet printer head 118. Also, the inkjet printer 112 can be configured to include any number of cartridges 114, lines 116, or printer heads 118. Usually, the inkjet printer 112 includes at least one binder cartridge.

The powder delivery system 120 has at least one powder delivery chamber 122 that provides a chamber for a powder delivery piston 124. In combination, the powder delivery chamber 122 and powder delivery piston 124 cooperate to contain the metal and/or ceramic powder 126. The powder delivery piston 124 is configured to move upward as shown by the arrows after each layer of powder is used in the direct inkjet printing process.

The roller 140 is depicted to be a conventional rolling object, such as one rolling part of a calender, which can roll a layer 142 of the powder 126 from the powder delivery system 120 to the fabrication system 130. However, a squeegee or other similar mechanical instruments can be used to scrape or move a top layer of powder from the powder delivery system 120 to the fabrication system 130.

The fabrication system 130 has at least one fabrication chamber 132 that provides a chamber for a fabrication piston 134. In combination, the fabrication chamber 132 and fabrication piston 134 cooperate to contain the endoprosthesis 136 as it is being fabricated. The fabrication piston 124 is configured to move downward as shown by the arrows after each layer of powder is deposited onto the endoprosthesis 136 and fixed by a binder solution contained in an inkjet cartridge 114.

As shown, the endoprosthesis 136 is built in the fabrication chamber 132 on a substrate or platform situated on or integral with the fabrication piston 134. As such, the powder delivery piston 124 rises so that a top layer 142 of the powder 126 in the powder delivery chamber 122 is rolled by the roller 140 into the fabrication chamber 132. After the top layer 142 of the powder 126 is deposited onto the fabrication piston 134, the inkjet printing head 118 selectively deposits or inkjet prints a binder fluid to cure or otherwise fuse the powder 126 together in the desired areas. Unbound powder can remain to support the part or bound layer of the 136 endoprosthesis that has been hardened. After hardening the bound layer, the fabrication piston 134 is lowered, more powder 126 is added from the powder delivery chamber 122 to the fabrication chamber 134 and leveled, and the process is repeated. Typical layer thicknesses are on the order of 100 microns. During this procedure, the deposition and binding can be configured so as to leave pores 138 within the endoprosthesis 136. When finished, the endoprosthesis 136 is considered to be a green body having pores 138 that is then removed from the unbound ceramic powder, and excess unbound powder is blown off or washed away. Also, the removal of the unbound powder can form the pores 138.

The printed body can then be cured (e.g., sintered) or otherwise finished into an endoprosthesis. While the printed body can be partially cured or hardened during printing, an additional curing step can be advantageous to finish the product. Optionally, such curing or finishing can be performed at low temperatures by immersing the printed body into a curing solution or hardening solution that causes the powder to react and harden to its fully hardened state.

In one embodiment, a metal printing process (MPP) can be used in a method of manufacturing the porous body. The MPP technique produces three-dimensional objects from powder material, utilizing photo-masking and electrostatic attraction, similar to a photocopy machine. The MPP technique uses the same fundamental methods as a photocopy machine to build solid objects; on a layer-by-layer basis. MPP is able to fabricate porous metal bodies with controlled porosity. MPP techniques are well known in the art.

In one embodiment, each layer is deposited on a building table where it is sintered with the aid of electric discharge sintering or microwaves. Sintering happens when particles fuse by atomic transport events below their melting points. Sintering enables a manufacturer to choose amongst a large assortment of appropriate powders to use in building endoprostheses. Common powders for sintering include iron and steel as well as more exotic materials such as titanium, nickel-based superelastic alloys, and the like. Sintering needs to be achieved in both materials simultaneously without distortion or the formation of defects. Co-sintering requires that the two materials follow the same shrinkage pathway, even though they may exhibit differences in basic properties. Additionally, the inkjet printing and metal printing processes can be combined and features thereof can be used together so that the direct rapid prototyping procedures can utilize for non-metals, such as ceramics. When ceramics are used, the process can be considered a powder printing process.

D. Depositing Matrix/Agent

The elution rate controlling matrix can be deposited in the pores of the porous body by various processes well known in the art for applying polymers to substrates. The polymer matrix that is deposited into the pores usually includes the active agent mixed therein. However, the active agent can be absorbed into the matrix after being deposited into the pores. Alternatively, the active agent can be deposited into the pore and then covered with the polymeric matrix. For example, some methods of depositing the polymeric matrix and/or the active agent into the pores can be conducted by spraying, dipping, rolling, brush application, vapor phase deposition, sputtering, and the like. Typically, a polymeric solution is deposited into the pores and cured and/or dried. There are many additional possible and well known ways in the art, of incorporating the polymer and/or active agents substantially within the pores of a porous body.

For example, the active agent can be incorporated into a polymer solution that cures into the polymer matrix and then is applied into the pores of the endoprosthesis and allowed to cure. Alternatively, incorporation of the active agent into the polymer matrix can be carried out by dipping the endoprosthesis having the polymer matrix disposed within the pores into a solution containing the active agent for a sufficient period of time (such as, for example, five minutes) and then drying the endoprosthesis for a sufficient period of time (e.g., 10, 15, or 30 minutes).

E. Additional Manufacturing Techniques

Various processes of producing porous coatings on substrates is well known in the art and has been described in numerous patents and publications. Commercial operations providing technology to apply porous coatings exist as well. For an endoprosthesis, the porous coating can be applied to the supporting structure from which the endoprosthesis is eventually cut, or to the shaped endoprosthesis. A porous coating may be applied to the supporting structure at the luminal side and/or the side opposite of the lumen.

The elution rate controlling matrix with or without the active agent can be disposed into the pores of the porous body with solutions that contain the polymer that is cured or solidified to form the matrix. A vacuum may be applied to the porous body to remove trapped air from the pores in order increase the loading efficiency. Also, a wiping step may remove excess polymeric material from outside the pores.

For example, a supporting structure can be coated with a porous metal coating according to U.S. Pat. No. 4,612,160, and an endoprosthesis is cut from the supporting structure having the porous coating thereon. The endoprosthesis is submerged in a mixture of poly-lactide-co-glycolide and zotarolimus (e.g., a rapamycin analog, ABT-578) in acetone (10% polymer, 10% drug), and a vacuum is applied to remove air from the pores before the endoprosthesis is removed from the solution. The excess liquid is blown off of the endoprosthesis with a stream of gas directed axially to the endoprosthesis and the endoprosthesis is dried. The process may be repeated several times to build up a sufficient quantity of drugs and polymer in the pores, provided the exposure time to the drug polymer solution is sufficiently short that the pre-deposited drug does not dissolve. As an alternative to the air removal of excess drug and polymer, a wipe with a brush or other wiping device constructed to leave the drug and polymers in the pores undisturbed can be used.

In another example, a supporting structure can be coated with a porous metal coating according to U.S. Pat. No. 4,612, 160, and an endoprosthesis is cut from the supporting structure having the porous coating thereon. The endoprosthesis is mounted on a snug-fitting mandrel. The endoprosthesis-mandrel assembly is coated with a polymer-drug mixture using an extrusion technology analogous to wire coating, with high pressure on the mixture to force it into the pores. A die of a size that allows little or no polymer to remain or be deposited on the outer diameter of the endoprosthesis is used. The "islands" of drug-polymer mix that get stuck on the outside of the endoprosthesis can be easily removed after cooling of the mixture.

There are multiple techniques for applying a porous layer to endoprostheses. For example, the sputter deposition process can be used to create nanostructured materials that possess continuous open porosity. In general, structural morphologies found for conventionally sputtered coatings can range from porous columnar to dense polycrystalline. The transition in morphology through four zones of growths occurs with increasing substrate temperature and sputter gas pressure. A three-dimensional polycrystalline deposit with continuous open porosity is produced under conditions of increased working gas pressure and a substrate temperature at approximately half its absolute melting point.

One method for applying a porous layer to an endoprostheses, as described by Astro Met, Inc., includes a complete porous metal beaded coating in titanium and cobalt-chromoly materials being applied to medical devices.

Another method for applying a porous metal layer to a dense metal substrate is described in U.S. Pat. No. 6,945,448. The method includes the following: providing a structured porous layer; providing a dense metal substrate; providing a binding mixture; applying the binding mixture to the exterior of the substrate; placing the porous layer against the substrate such that the binding mixture is disposed therebetween, thus forming an assembly; and heat treating the assembly in order to metallurgically bond the porous layer to the substrate.

Another method for applying a porous metal layer to a supporting structure is described in US Patent Application No. 20050048193. This method includes layers built up of strata of flat or non-flat layers. A layer with external or internal discontinuities or a layer of non-planar form, or characterized by a layer of regularly arranged cells whether integral or formed individually, or by conjunction of separate strips (e.g. a honeycomb structure).

Yet another method that would be utilized for manufacturing a porous layer, in part, is the MPP technique. For example, using the MPP technique, a porous coating to a medical device is manufactured when a ceramic and metal are combined; the ceramic functions as the insulator and the metal provides electrical interconnections in a three-dimensional array.

Certain exemplary polymers used in the methods for applying a porous coating include, but are not limited to, Dexon, Vicryl, natural rubber, silicone rubbers, medical grade poly-dimethylsiloxanes, and silicone-carbonate copolymers. Non-limiting examples of other suitable polymers include EPDM rubbers, nylon, and epoxies. Polymers including pendant phosphoryl groups are disclosed in U.S. Pat. Nos. 5,705,583 and 6,090,901 and 6,083,257 which are all incorporated herein by reference.

IV. Method of Treating and Preventing Diseases

In one embodiment, the invention relates to methods of using the medical device for treating and/or preventing at least one animal disease. The medical device has at least one elution rate controlling material and also provides an effective amount of at least one agent within at least one porous material associated with the medical device. The pores of the at least one porous layer are dimensioned and configured to house the elution rate controlling material and the agents for controlled release applications of agents into an animal for the treatment and prevention of diseases.

In one embodiment, the present invention includes a method of treating and/or preventing a disease in an animal. Such as method can include the following: providing a medical device configured and dimensioned to be used within a body of an animal, as described herein; deploying the medical device into the body of the animal; and allowing the active agent to elute from the pores into the body of the animal, where the elution rate controlling matrix controls the elution of the active agent from the pores. Accordingly, the medical device can be placed into or in contact with a body or fluid of an animal. This can include placing the medical device within the vascular system of an animal. The medical device can then elute a therapeutically effective amount of the active agent to treat and/or prevent a disease in which said active agent is useful as a therapy. For example, the medical device can treat a vascular disease, such as restenosis.

When used in the above or other treatments, a therapeutically effective amount of one of the active agent may be employed. It will be understood, however, that the total daily usage of the active agents will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; route of administration; and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

In one embodiment, the active agent can be delivered in an amount that generates a local concentration of the analog in the tissues, cells, cellular matrices, body fluids, blood, or the like adjacent or proximal to the endoprosthesis. This can include achieving a concentration of the active agent that inhibits and/or treats a disease in which the active agent can be used as part of a therapeutic regimen. For example, the active agent (e.g., rapamycin analog) can be delivered to produce a local concentration of about 10 pg/ml to about 10 mg/ml. More preferably, active agent can produce a local concentration of about 100 pg/ml to about 1 mg/ml. Even more preferably, the active agent can produce a local concentration of about 1 ng/ml to about 100 ug/ml. Still more preferably, the active agent can produce a local concentration of about 10 ng/ml to about 10 ug/ml. Still more preferably, the active agent can produce a local concentration of about 100 ng/ml to about 1 ug/ml. Most preferably, the active agent can produce a local concentration of about 500 ug/ml.

In one embodiment, the active agent can be delivered in an amount that generates a sustained local concentration of the active agent in the tissues, cells, cellular matrices, body fluids, blood, or the like proximate to the medical device that is expressed as molarity. As such, delivery of the active agent (e.g., rapamycin analog) can produce a sustained local concentration of about 10 pM to about 10 mM. More preferably, the active agent can produce a sustained local concentration of about 100 pM to about 1 mM. Even more preferably, the active agent can produce a sustained local concentration of about 1 nM to about 100 uM. Still more preferably, the active agent can produce a sustained local concentration of about 10 nM to about 10 uM. Still more preferably, the active agent can produce a sustained local concentration of about 100 nM to about 1 uM. Most preferably, the active agent can produce a sustained local concentration at about 300 nM.

The total daily dose of the active agent eluted from the medical device into a human or lower animal may range from about 0.01 to about 10 mg/kg/day. For the purposes of local delivery from a stent, the daily dose that a patient will receive depends on the length of the stent. For example, a 15 mm coronary stent may contain a drug in an amount ranging from about 1 to about 120 mg and may deliver that drug over a time period ranging from several hours to several weeks.

In some instances, the elution rate controlling matrix can be configured to modulate the rate of elution of the active agent, which can include a substantially constant or steady-state rate. Also, this can include being released with or without an initial burst followed by 0, 1st, or 2nd order delivery kinetics.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope. Additionally, all references recited herein are included herein in their entirety by specific reference.

What is claimed is:

1. A medical device for controlling the release of an active agent, the medical device comprising:
   a supporting structure configured and dimensioned to be used within a body of a human or an animal;
   a porous body disposed on and at least partially covering the supporting structure, said porous body being constructed of a first biocompatible material and said porous body having a plurality of pores, the first biocompatible material being a metal, a ceramic, or a combination of metal and ceramic;
   a therapeutically effective amount of an active agent disposed within the pores; and
   an elution rate controlling matrix within the pores to contain the active agent, said matrix comprising a second biocompatible material that controls an elution rate of the active agent from the pores; and
   wherein the second biocompatible material is biodegradable and degrades in a period less than five years upon exposure to a physiological solution, and each pore comprises an upper volume and a lower volume, the active agent occupies the upper volume and the lower volume, and the upper volume is separated from the lower volume by an intermediate layer of the matrix.

2. The medical device according to claim 1, wherein the porous body has a thickness ranging from about 10 nanometers to about 1 millimeter, and the pores have a diameter from about 10 nanometers to about 1 millimeter.

3. The medical device according to claim 1, wherein the medical device is selected from the group consisting of endoprostheses, drug delivery stents, drug delivery catheters, grafts, drug delivery balloons, guidewires, orthopedic implants, dental implants, fixation screws, indwelling catheters, ocular implants, pharmacotherapeutic implants, blood-contacting components of extracorporeal devices, staples, filters, needles, tubes, coils, wires, clips, screws, sensors, plates, conduits, portions thereof, and combinations thereof.

4. The medical device according to claim 1, wherein said second biocompatible material degrades between about one hour and several weeks upon exposure to the physiological solution.

5. The medical device according to claim 1, wherein said second biocompatible material comprises at least one polymeric material selected from the group consisting of phosphorylcholines, phosphorylcholine linked macromolecules, polyesters, polyanhydrides, polyphosphazenes, polyacrylates, poly(lactide-co-glycolides) (PLGA), polylactic acids (PLA), poly(hydroxybutyrates), poly(hydroxybutyrate-co-valerates), polydioxanones (PDO), polyorthoesters, polyglycolic acids (PGA), polycaprolactones (PCL), poly(glycolic acid-co-trimethylene carbonates), polyphosphoesters, polyphosphoester urethanes, poly(amino acids), cyanoacrylates, poly(trimethylene carbonate), poly(iminocarbonate), polyalkylene oxalates, polyiminocarbonates, aliphatic polycarbonates, fibrins, fibrinogens, celluloses, starchs, collagens, polycarbonate urethanes, plasticized polyethylene terephthalates, polyethylene terepthalates, polybutylene terepthslate-co-PEG, PCL-co-PEG, PLA-co-PEG-polyamides, copolymers thereof, polymer derivatives thereof, and combinations thereof.

6. The medical device according to claim 1, wherein said active agent comprises at least one member of the group consisting of analgesics, antipyretics, antiasthamatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds or hormones, and combinations thereof.

7. The medical device according to claim 1, wherein said active agent comprises at least one member of the group consisting of rapamycin, rapamycin analogs, zotarolimus, sirolimus, everolimus, dexamethasone, prednisone, hydrocortisone, estradiol, acetaminophen, ibuprofen, naproxen, sulidac, heparin, taxol, paclitaxel, and combinations thereof.

8. The medical device according to claim 1, wherein the active agent comprises a first active agent composition and a second active agent composition differrent in composition from the first active agent composition, and the first active agent composition and the second active agent composition are separated from each other by being contained in separate groups of the microspheres disposed within the pores.

9. The medical device according to claim 1, wherein the upper volume of the agent is covered by an outer layer of the matrix.

10. The medical device according to claim 1, wherein the active agent comprises a first active agent composition and the second active agent composition different in composition from the first active agent composition, the intermediate layer separates the first active agent compostion from the second active agent composition, the first active agent composition is contained in the upper volume, and the second active agent compostion is contained in the lower volume.

11. The medical device according to claim 1, wherein the supporting structure is configured and dimensioned as a stent and is configured to expand from a delivery orientation to a deployed orientation.

12. The medical device according to claim 1, wherein said first biocompatible material is a metal.

13. The medical device according to claim 1, wherein said first biocompatible material is a ceramic.

\* \* \* \* \*